(12) United States Patent
Chen et al.

(10) Patent No.: US 12,297,293 B2
(45) Date of Patent: May 13, 2025

(54) PEPTIDE COMPOUNDS TARGETING PD-1 RECEPTOR AS WELL AS PREPARATION AND APPLICATIONS THEREOF

(71) Applicant: NANTONG UNIVERSITY, Jiangsu (CN)

(72) Inventors: Gang Chen, Jiangsu (CN); Long Zhao, Jiangsu (CN); Yayu Zhao, Jiangsu (CN); Ying Chen, Jiangsu (CN); Hao Luo, Jiangsu (CN); Yonghui Zhang, Jiangsu (CN); Jinhuan Wei, Jiangsu (CN)

(73) Assignee: NANTONG UNIVERSITY, Jiangsu (CN)

( * ) Notice: Subject to any disclaimer, the term of this patent is extended or adjusted under 35 U.S.C. 154(b) by 0 days.

(21) Appl. No.: 18/568,525

(22) PCT Filed: Jun. 1, 2022

(86) PCT No.: PCT/CN2022/096623
§ 371 (c)(1),
(2) Date: Dec. 8, 2023

(87) PCT Pub. No.: WO2022/257831
PCT Pub. Date: Dec. 15, 2022

(65) Prior Publication Data
US 2024/0336652 A1  Oct. 10, 2024

(30) Foreign Application Priority Data
Jun. 10, 2021 (CN) .......................... 202110651404.7

(51) Int. Cl.
C07K 7/06 (2006.01)
A61K 38/00 (2006.01)
A61P 29/00 (2006.01)
C07K 1/04 (2006.01)
C07K 1/06 (2006.01)
C07K 1/20 (2006.01)

(52) U.S. Cl.
CPC ................ *C07K 7/06* (2013.01); *A61P 29/00* (2018.01); *C07K 1/04* (2013.01); *C07K 1/061* (2013.01); *C07K 1/20* (2013.01); *A61K 38/00* (2013.01)

(58) Field of Classification Search
CPC .. C07K 7/06; C07K 1/04; A61P 29/00; A61K 38/00
See application file for complete search history.

(56) References Cited

U.S. PATENT DOCUMENTS

2008/0039404 A1    2/2008  Hruby et al.

FOREIGN PATENT DOCUMENTS

| CA | 1340636 C | 7/1999 | |
|---|---|---|---|
| CN | 110183514 A | 8/2019 | |
| CN | 111606976 A | 9/2020 | |
| CN | 112079924 A | * 12/2020 | ..... A61K 39/001102 |
| CN | 113416232 A | 9/2021 | |

* cited by examiner

*Primary Examiner* — Amber D Steele

(57) ABSTRACT

A peptide compound targeting a PD-1 receptor includes: a compound 1, a compound 2, a compound 3, a compound 4 and a compound 5; wherein the compounds 1-5 comprise amino acid sequences identical to SEQ ID NO: 1-5, respectively. A method for preparing the peptide compound targeting the PD-1 receptor includes steps of: using a solid-phase synthesis method for coupling amino acids of the compounds 1-5 to a solid-phase resin sequentially according to peptide sequences, and obtaining a target compound after cleavage by a cutting reagent, freeze-drying, and preparative purification. A method for preparing analgesic drugs includes using the peptide compound targeting the PD-1 receptor. The compounds 1-5 are capable of binding to PD-1, and have significant inhibitory effects on inflammatory pain and visceral pain under intrathecal administration; they are simple to synthesize, easy to be purified, and conducive to large-scale synthesis.

1 Claim, 3 Drawing Sheets
Specification includes a Sequence Listing.

SEQUENCE LISTING

<160> NUMBER OF SEQ ID NOS: 5

<210> SEQ ID NO 1
<211> LENGTH: 9
<212> TYPE: PRT
<213> ORGANISM: Artificial Sequence

```
<220> FEATURE:
<223> OTHER INFORMATION: sequence is synthesized

<400> SEQUENCE: 1

Val Tyr Arg Cys Met Ile Ser Tyr Gly
1               5

<210> SEQ ID NO 2
<211> LENGTH: 9
<212> TYPE: PRT
<213> ORGANISM: Artificial Sequence
<220> FEATURE:
<223> OTHER INFORMATION: sequence is synthesized

<400> SEQUENCE: 2

Tyr Arg Cys Met Ile Ser Tyr Gly Gly
1               5

<210> SEQ ID NO 3
<211> LENGTH: 9
<212> TYPE: PRT
<213> ORGANISM: Artificial Sequence
<220> FEATURE:
<223> OTHER INFORMATION: sequence is synthesized

<400> SEQUENCE: 3

Met Ile Ser Tyr Gly Gly Ala Asp Tyr
1               5

<210> SEQ ID NO 4
<211> LENGTH: 9
<212> TYPE: PRT
<213> ORGANISM: Artificial Sequence
<220> FEATURE:
<223> OTHER INFORMATION: sequence is synthesized

<400> SEQUENCE: 4

Ser Tyr Gly Gly Ala Asp Tyr Lys Arg
1               5

<210> SEQ ID NO 5
<211> LENGTH: 9
<212> TYPE: PRT
<213> ORGANISM: Artificial Sequence
<220> FEATURE:
<223> OTHER INFORMATION: sequence is synthesized

<400> SEQUENCE: 5

Tyr Gly Gly Ala Asp Tyr Lys Arg Ile
1               5
```

PEPTIDE COMPOUNDS TARGETING PD-1 RECEPTOR AS WELL AS PREPARATION AND APPLICATIONS THEREOF

BACKGROUND OF THE PRESENT INVENTION

Field of Invention

The present invention relates to biomedical technology, and more particularly to a class of peptide compounds targeting a PD-1 receptor, as well as preparation and applications thereof.

Description of Related Arts

In recent years, chronic pain, including low back pain, arthritis, persistent postoperative pain, fibromyalgia, and neuropathic diseases, is a very common social problem today, and more than 20% of adults in developed countries are suffering from chronic pain (J. Neurosci. 2021, 41, 855-865). Chronic pain, although not fatal, is not well-treated and poses a serious social and economic burden. Although signaling between immune cells, glial cells, and neurons is now considered indispensable for triggering and maintaining chronic pain, the vast majority of therapeutic drugs still target neurons only.

Conventionally, opioids have been widely used in the clinical treatment of non-cancer chronic pain, but the inevitable side effects of opioids, such as drug tolerance, physical and mental dependence, inhibition of gastrointestinal function, nausea, sedation, agitation, hallucinations, and impairment of locomotor function, are the main problems hindering their use in clinical treatment. Thus, there is an urgent need to develop new analgesic drugs that are effective and safe.

Programmed death ligand (PD-L1 also known as B7-H1 or CD274), a member of the B7 family, is widely expressed in humans with cancer. In the microenvironment of tumors, PD-L1 is able to bind to PD-1 as a co-inhibitory checkpoint molecule and participate in immune regulation. Conventionally, a large amount of PD-1/PD-L1 pathway research focuses on T-lymphocyte tolerance and activation and polarization with macrophages in tumor immune escape. In recent years, functions of PD-L1/PD-1 besides tumor therapy have been progressively reported, including murine lupus, colitis, collagen-induced arthritis, and brain injury.

Recent studies have found that the PD-L1/PD-1 pathway has excellent efficacy in acute and chronic pain after nerve injury, and injection of exogenous PD-L1 can significantly increase the pain threshold of normal mice (Nat. Neurosci. 2017, 20, 917-926). Furthermore, the analgesic effect of morphine can be significantly enhanced by the co-administration of PD-L1 and low-dose morphine, and thus reduce the side effects caused by high doses of morphine (Sci. Transl. Med. 2020, 12, eaaw6471). Therefore, PD-1 targeting has potential application in the development of new analgesic drugs.

SUMMARY OF THE PRESENT INVENTION

In response to problems or deficiencies in the prior art, an object of the present invention is to provide a class of peptide compounds targeting a PD-1 receptor, as well as preparation and applications thereof.

Accordingly, in order to accomplish the above objects, the present invention provides a peptide compound targeting a PD-1 receptor, comprising: a compound 1, a compound 2, a compound 3, a compound 4 and a compound 5; wherein the compounds 1-5 comprise amino acid sequences identical to SEQ ID NO: 1-5, respectively:

```
SEQ ID NO: 1:
Val Tyr Arg Cys Met Ile Ser Tyr Gly;

SEQ ID NO: 2:
Tyr Arg Cys Met Ile Ser Tyr Gly Gly;

SEQ ID NO: 3:
Met Ile Ser Tyr Gly Gly Ala Asp Tyr;

SEQ ID NO: 4:
Ser Tyr Gly Gly Ala Asp Tyr Lys Arg;
and

SEQ ID NO: 5:
Tyr Gly Gly Ala Asp Tyr Lys Arg Ile.
```

The present invention also provides a method for preparing the peptide compound targeting the PD-1 receptor, comprising steps of: (1) using a solid-phase synthesis method for coupling amino acids of the compounds 1-5 to a solid-phase resin sequentially according to peptide sequences, and (2) obtaining a target compound after cleavage by a cutting reagent, freeze-drying, and preparative purification.

Preferably, the step (1) comprises specific steps of:
(1-1) dissolving and expanding wang resin in dichloromethane, compressing the wang resin in anhydrous methanol, and washing the wang resin with N,N-dimethylacetamide, so as to using the wang resin as a solid phase carrier during solid phase synthesis;
(1-2) adding an appropriate amount of a Fmoc group removal reagent into the pretreated wang resin for resin amino group deprotection; using a 20% hexahydropyridine N,N-dimethylformamide solution as a removal reagent for an amino protection group 9-fluorenylmethoxycarbonyl, and performing elution 3 times with 5 min for each time; after elution, washing with N, N-dimethylformamide, and performing a resin/peptide resin indene test; and
(1-3) using a solid-phase synthetic condenser, starting from a first amino acid at a C-terminal end of the peptide sequences of the compounds 1-5, and condensing the amino acids sequentially onto the peptide resin; wherein an amount of the amino acids is 3 times an amount of substance of the peptide resin, and a time period for amino acid condensation is 1-1.5 h; the condensation is carried out under an inert gas atmosphere to obtain crude peptide resin; the solid-phase synthetic condenser is N,N-diisopropylethylamine/1-hydroxybenzotriazole/O-benzotriazole-tetramethyluronium hexafluorophosphate, and an amount of the solid-phase synthetic condenser is 3-6 times the amount of the peptide resin.

Preferably, the step (2) comprises specific steps of:
(2-1) repeatedly dissolving, expanding and compressing the crude peptide resin obtained in the step (1) by dichloromethane/anhydrous methanol;
(2-2) cutting crude peptide from the crude peptide resin with the cutting reagent, then spin-drying, extracting, and freeze-drying to obtain desired crude peptide; wherein the cutting reagent required for the cleavage of the crude peptide resin comprises trifluoroacetic acid, triisopropylsilane, and bisdistilled water, wherein a volume ratio of trifluoroacetic acid:triisopropylsilane:bisdistilled water is =95:2.5:2.5; and (2-3) freeze-drying and purifying the crude peptide resin by reverse-HPLC preparative column to obtain white solid compounds 1-5 in 35%-45% yields, thereby obtaining the peptide compound targeting the PD-1 receptor.

The present invention also provides a method for preparing analgesic drugs, comprising using the peptide compound targeting the PD-1 receptor.

Preferably, the analgesic drugs comprise drugs for treating inflammatory pain and visceral pain.

Preferably, the analgesic drugs are capable of intrathecal administration, subcutaneous administration, caudal vein administration, lateral ventricular administration, intraperitoneal administration or oral administration.

Preferably, therapeutic target of the analgesic drugs is the PD-1 receptor.

Preferably, the peptide compound may be one of the compound 1, the compound 2, the compound 3, the compound 4 and the compound 5.

The beneficial effects of the above technical solution of the present invention are as follows:

(1) The present invention provides small molecule peptide: the compounds 1-5 are five compounds with Amber scores in the [−90,−80] region obtained by molecular docking technology from peptide libraries; these five compounds are capable of binding to PD-1, and have significant inhibitory effects on inflammatory pain and visceral pain under intrathecal administration; they are simple to synthesize, easy to be purified, and conducive to large-scale synthesis.

(2) The short peptide sequences of the compounds 1-5 of the present invention are easier to use as chemical templates for modification and transformation to improve their pharmacological and pharmacokinetic properties than PD-L1.

(3) Based on previous research, the present invention identifies a novel class of small molecule peptides with partially similar characteristics to PD-L1, which can target PD-1 and have significant analgesic effects on formalin-induced inflammatory pain and acetic acid-induced visceral pain, showing potential clinical application value.

(4) Compared with conventional opioids, the compounds 1-5 of the present invention target the PD-1 receptor, so as to effectively circumvent opioid-related side effects induced by activation of opioid receptors, which are more advantageous in terms of drug safety, showing potential for clinical application.

DETAILED DESCRIPTION OF THE PREFERRED EMBODIMENT

Figure 1:
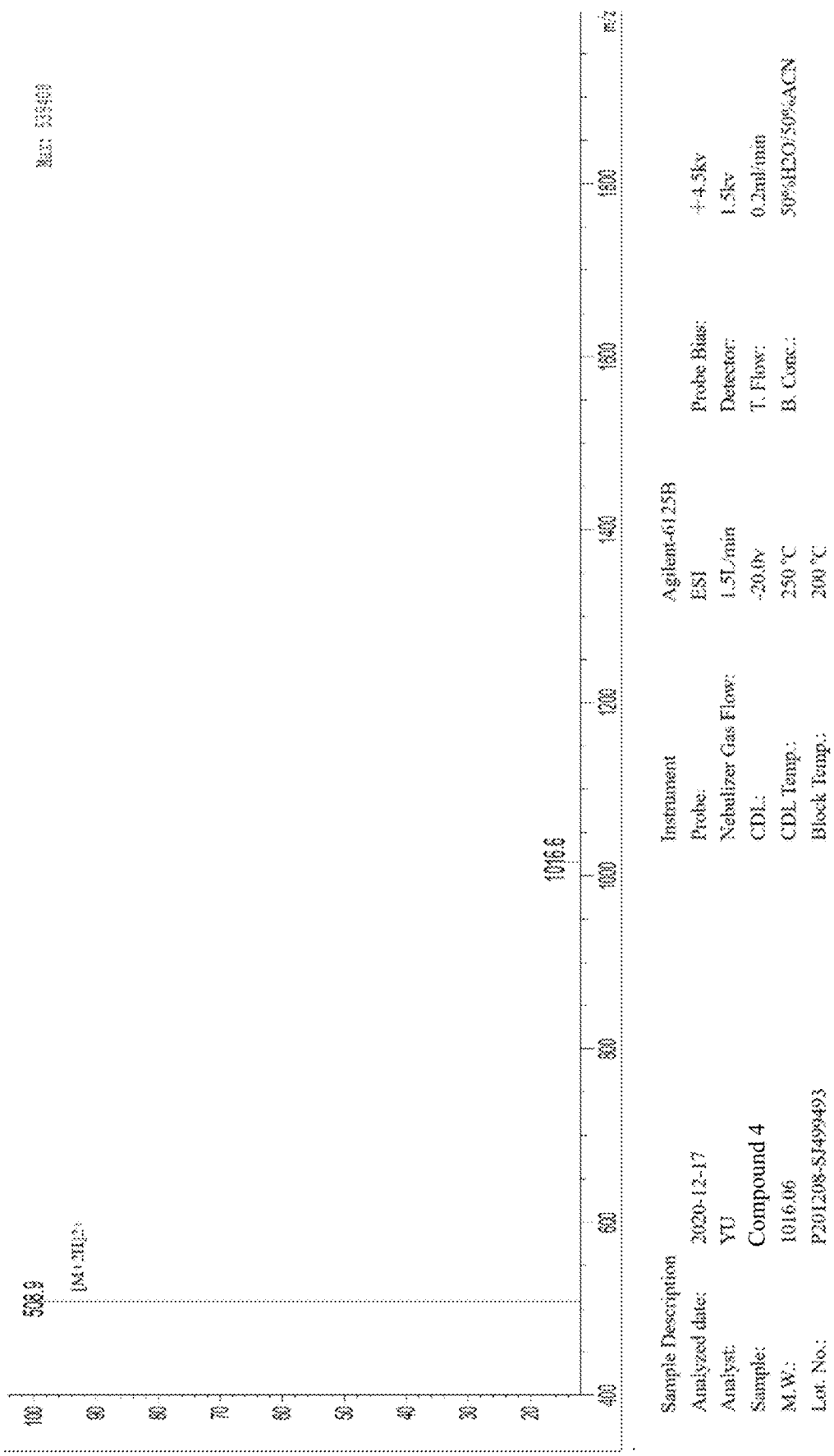
FIG. 1 is an ESI-MS spectrum of a compound 4 according to an embodiment of the present invention.

In order to make the technical problems to be solved, the technical solutions and the advantages clearer, the present invention will be further illustrated in conjunction with specific embodiments.

Embodiment 1: Solid-Phase Synthesis of Compounds 1-5

The compounds 1-5 of the present invention are synthesized by Fmoc-solid phase synthesis method, and wang-resin is used as a solid phase carrier. The removal reagent for an amino protecting group 9-fluorenylmethoxycarbonyl (Fmoc) is 20% hexahydropyridine N,N-dimethylformamide solution. A condensation reagent required for peptide chain extension is N,N-diisopropylethylamine/1-hydroxybenzotriazole/O-benzotriazole-tetramethyluronium hexafluorophosphate, and an amount required is 3-6 times the amount of resin used. A cutting agent required for cutting crude peptide from the resin is a mixture of trifluoroacetic acid/triisopropylsilane/bisdistilled water in a volume ratio of 95:2.5:2.5. Components and ratios of the condensation reagent, the Fmoc removal reagent, and the indene detection reagent in the present invention are known to those skilled in the art.

1) Synthesis of Compound 1 weighing wang resin, dissolving and expanding in dichloromethane, compressing in anhydrous methanol, and washing with N,N-dimethylacetamide; adding an appropriate amount of a Fmoc group removal reagent into the pretreated wang resin for resin amino group deprotection; using N,N-diisopropylethylamine/1-hydroxybenzotriazole/O-benzotriazole-tetramethyluronium hexafluorophosphate as a solid-phase synthetic condenser, sequentially condensing N-Fmoc-glycine, N-Fmoc-O-tert-butyl-L-tyrosine, N-Fmoc-L-serine, N-Fmoc-L-isoleucine, N-Fmoc-L-methionine, N-(9-Fmoc)-S-trityl-L-cysteine, N-(9-Fmoc)-NG-2,2,4,6,7-pentamethylbenzofuran-5-sulfonyl-L-arginine, N-Fmoc-O-tert-butyl-L-tyrosine, and N-Fmoc-L-valine onto the peptide resin; dissolving and expanding the crude peptide resin in dichloromethane, compressing with anhydrous methanol, and repeating the step 3 times before drying; cutting the crude peptide from the resin using trifluoroacetic acid/triisopropylsilane/bidistilled water, then spin-drying, extracting, and freeze-drying to obtain desired crude peptide comprising an amino acid sequence identical to SEQ ID NO: 1; and then purifying by RP-HPLC preparative column, wherein a yield is 38%.

Identification results of mass spectrometry and purity analysis are shown in Table 1.

2) Synthesis of Compound 2 performing same resin pretreatment and Fmoc group removal process as those of the compound 1; using N,N-diisopropylethylamine/1-hydroxybenzotriazole/O-benzotriazole-tetramethyluronium hexafluorophosphate as a solid-phase synthetic condenser, sequentially condensing N-Fmoc-glycine, N-Fmoc-glycine, N-Fmoc-O-tert-butyl-L-tyrosine, N-Fmoc-L-serine, N-Fmoc-L-isoleucine, N-Fmoc-L-methionine, N-(9-Fmoc)-S-trityl-L-cysteine, N-(9-Fmoc)-NG-2,2,4,6,7-pentamethylbenzofuran-5-sulfonyl-L-arginine, and N-Fmoc-O-tert-butyl-L-tyrosine onto the peptide resin; dissolving and expanding the crude peptide resin in dichloromethane, compressing with anhydrous methanol, and repeating the step 3 times before drying; cutting the crude peptide from the resin using trifluoroacetic acid/triisopropylsilane/bidistilled water, then spin-drying, extracting, and freeze-drying to obtain desired crude peptide comprising an amino acid sequence identical to SEQ ID NO: 2; and then purifying by RP-HPLC preparative column, wherein a yield is 35%.

Identification results of mass spectrometry and purity analysis are shown in Table 1.

3) Synthesis of Compound 3 performing same resin pretreatment and Fmoc group removal process as those of the compound 1; using N,N-diisopropylethylamine/1-hydroxybenzotriazole/O-benzotriazole-tetramethyluronium hexafluorophosphate as a solid-phase synthetic condenser, sequentially condensing N-Fmoc-O-tert-butyl-L-tyrosine, N-Fmoc-L-aspartic acid-4-tert-butyl ester, N-Fmoc-alanine, N-Fmoc-glycine, N-Fmoc-glycine, N-Fmoc-O-tert-butyl-L-tyrosine, N-Fmoc-L-serine, N-Fmoc-L-isoleucine, and N-Fmoc-L-methionine onto the peptide resin; dissolving and expanding the crude peptide resin in dichloromethane, compressing with anhydrous methanol, and repeating the step 3 times before drying; cutting the crude peptide from the resin using trifluoroacetic acid/triisopropylsilane/bidistilled water, then spin-drying, extracting, and freeze-drying to obtain desired crude peptide comprising an amino acid sequence identical to SEQ ID NO: 3; and then purifying by RP-HPLC preparative column, wherein a yield is 45%.

Identification results of mass spectrometry and purity analysis are shown in Table 1.

4) Synthesis of Compound 4 performing same resin pretreatment and Fmoc group removal process as those of the compound 1; using N,N-diisopropylethylamine/1-hydroxybenzotriazole/O-benzotriazole-tetramethyluronium hexafluorophosphate as a solid-phase synthetic condenser, sequentially condensing N-Fmoc-L-isoleucine, N'-[(2,3-dihydro-2,2,4,6,7-pentamethylbenzofuran-5-yl) sulfonyl]-N-Fmoc-L-arginine, N-alpha-Fmoc-N-epsilon-tert-butoxycarbonyl-L-lysine, N-Fmoc-O-tert-butyl-L-tyrosine, N-Fmoc-L-aspartic acid-4-tert-butyl ester, N-Fmoc-alanine, N-Fmoc-glycine, N-Fmoc-glycine, and N-Fmoc-O-tert-butyl-L-tyrosine onto the peptide resin; dissolving and expanding the crude peptide resin in dichloromethane, compressing with anhydrous methanol, and repeating the step 3 times before drying; cutting the crude peptide from the resin using trifluoroacetic acid/triisopropylsilane/bidistilled water, then spin-drying, extracting, and freeze-drying to obtain desired crude peptide comprising an amino acid sequence identical to SEQ ID NO: 4; and then purifying by RP-HPLC preparative column, wherein a yield is 40%.

Identification results of mass spectrometry and purity analysis are shown in Table 1.

5) Synthesis of Compound 5 performing same resin pretreatment and Fmoc group removal process as those of the compound 1; using N,N-diisopropylethylamine/1-hydroxybenzotriazole/O-benzotriazole-tetramethyluronium hexafluorophosphate as a solid-phase synthetic condenser, sequentially condensing N'-[(2,3-dihydro-2,2,4,6,7-pentamethylbenzofuran-5-yl) sulfonyl]-N-Fmoc-L-arginine, N-alpha-Fmoc-N-epsilon-tert-butoxycarbonyl-L-lysine, N-Fmoc-O-tert-butyl-L-tyrosine, N-Fmoc-L-aspartic acid-4-tert-butyl ester, N-Fmoc-alanine, N-Fmoc-glycine, N-Fmoc-glycine, N-Fmoc-O-tert-butyl-L-tyrosine, and N-Fmoc-L-serine onto the peptide resin; dissolving and expanding the crude peptide resin in dichloromethane, compressing with anhydrous methanol, and repeating the step 3 times before drying; cutting the crude peptide from the resin using trifluoroacetic acid/triisopropylsilane/bidistilled water, then spin-drying, extracting, and freeze-drying to obtain desired crude peptide comprising an amino acid sequence identical to SEQ ID NO: 5; and then purifying by RP-HPLC preparative column, wherein a yield is 42%.

Identification results of mass spectrometry and purity analysis are shown in Table 1.

The peptide sequences, mass spectrometry identification, Amber scoring and purity analysis results of compounds 1-5 of the present invention are shown in Table 1:

TABLE 1

Physicochemical properties of compounds, Amber scoring and purity analysis

| name | peptide sequence | High-resolution mass spectra m/z [M + 2H]2+ calculated value | High-resolution mass spectra m/z [M + 2H]2+ detected value | Amber scoring | fineness (%) |
|---|---|---|---|---|---|
| SEQ ID NO: 1 | VYRCMISYG | 1091.3 | 1093 | −89.3 | 98 |
| SEQ ID NO: 2 | YRCMISYGG | 1049.2 | 1051 | −87.3 | 99 |
| SEQ ID NO: 3 | MISYGGADY | 976.1 | 977.8 | −84.2 | 99 |
| SEQ ID NO: 4 | SYGGADYKR | 1016.1 | 1017.8 | −83.3 | 97 |
| SEQ ID NO: 5 | YGGADYKRI | 1042.1 | 1044 | −80.1 | 98 |

The amino acid abbreviations of the present invention are shown in Table 2:

| Simplified form | Abbreviations | Full name |
|---|---|---|
| V | Val | valine |
| Y | Tyr | tyrosine |
| R | Arg | argnine |
| C | Cys | cysteine |
| M | Met | methionine |
| I | Ile | isoleucine |
| S | Ser | serine |
| G | Gly | glycine |
| A | Ala | alanine |
| D | Asp | aspartic acid |
| K | Lys | lysine |

Embodiment 2: DRG Neuronal Calcium Imaging Experiment

The inhibitory effect of compounds 1-5 on pain signaling was characterized by DRG neuronal calcium imaging, comprising the following steps:

performing acute isolation on 3-week-old female ICR mice, and extracting DRG in a sterile bench; lysing sequentially by collagenase A and trypsin; terminating trypsin lysis with a complete medium containing serum; centrifuging at 800r, discarding supernatant, and adding Neurobasal medium (containing 2% B27, Clutanine 1%, and 1% penicillin-streptomycin double antibody solution) and thoroughly mixing; then culturing in pre-prepared Petri dishes lined with PDL for 48 h; labeling DRG neurons with Flou-4/AM prior to the experiment, and pre-treating with different doses of the compounds 1-5/equivalent volume of HBSS before stimulating the DRG neurons with high K+ solution; and then detecting changes of intracellular free calcium ion concentration of DRG neurons under laser confocal.

Figure 2:
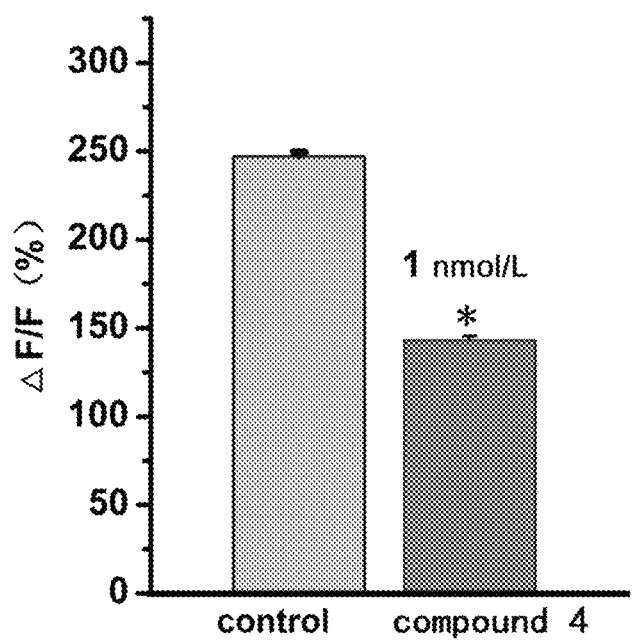
FIG. 2 illustrates inhibitory effect of the compound 4 on increase of free $Ca^{2+}$ in DRG cells induced by high K+ solution according to the embodiment of the present invention.

The experimental results of calcium imaging are shown in FIG. 2, wherein the DRG neurons pretreated with the compound 4 (1 nM) had a significant inhibitory effect on the increase of intracellular Ca2+ concentration induced by high K+, suggesting that the compound 4 can modulate pain signaling.

Embodiment 3: Formalin-Induced Inflammatory Pain Test

According to the present invention, placing ICR male mice in a weight range of 25-30 g in an observation room for 15 min, and injecting intrathecally with different doses of the compound 4 (5 nmol, 10 nmol, 30 nmol) or saline; after 5 min, injecting subcutaneously with 5% formalin (20 μl) through the plantar surface of the foot, and then immediately sending to the observation room; counting an accumulated time of pain behaviors (licking, biting, and flinging the injected foot) during the time period of 0-10 min and 10-45 min, respectively.

Figure 3:
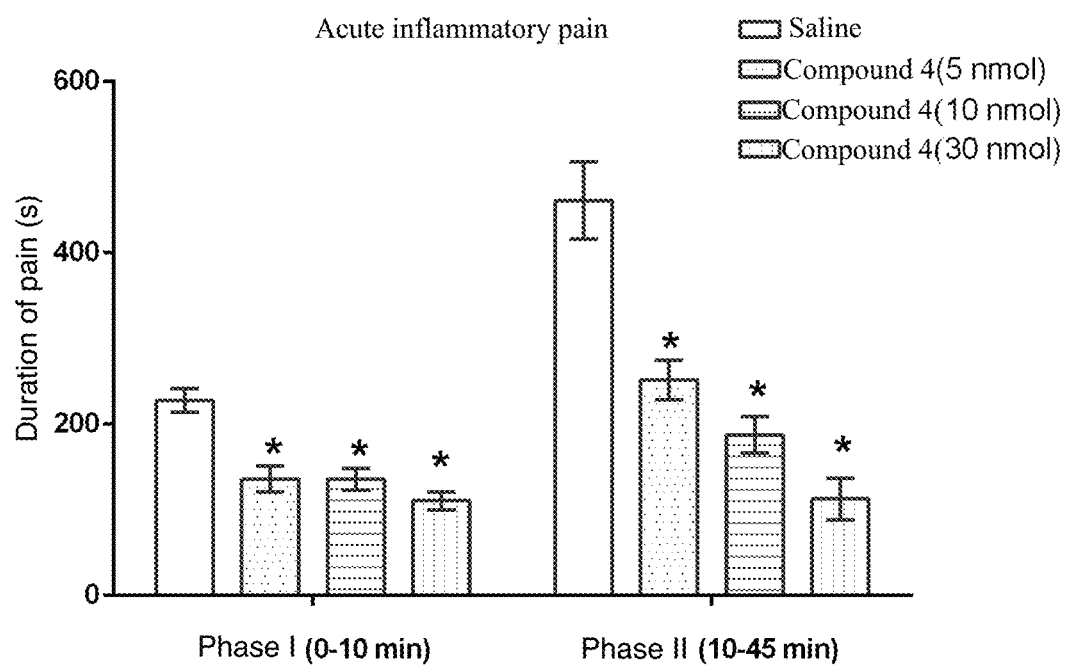
FIG. 3 illustrates analgesic effect after intrathecal injection of the compound 4 on acute inflammatory pain induced by formalin solution according to the embodiment of the present invention.

In a formalin-induced pain model of mice, after subcutaneous injection of formalin via the plantar surface of the foot, mice will exhibit pain behaviors such as licking, biting, paw-flinging, and leg stretching. 0-10 min after formalin injection is a phase I, which is mainly triggered by direct activation of injurious neurons; and 10-35 min is phase II, which is mainly triggered by formalin-induced inflammatory response. The experimental results are shown in FIG. 3. Compared with the control group, the compound 4 significantly shortened the pain behavior of mice such as licking, biting and flinging the injected foot in both phases, indicating that the compound 4 could reduce the pain behavior induced by activation of injurious neurons and inflammation. The inhibitory effect of the compound 4 on pain behavior triggered by formalin inflammatory factor was more significant than that triggered by direct activation of injurious neurons, wherein the ED50 (median effective dose) of the compound 4 for pain in phase II was 6.28 (5.34-7.39) nmol.

Embodiment 4: Acetic Acid-Induced Visceral Pain Test

According to the present invention, placing ICR male mice in a weight range of 25-30 g in an observation room for 15 min, and injecting intrathecally with different doses of the compound 4 (5 nmol, 10 nmol, 30 nmol) or saline; after 5 min, injecting intraperitoneally with 0.6% glacial acetic acid solution (10 mL/kg), and then sending to the observation room; counting the number of body writhing within 20 min.

Figure 4:
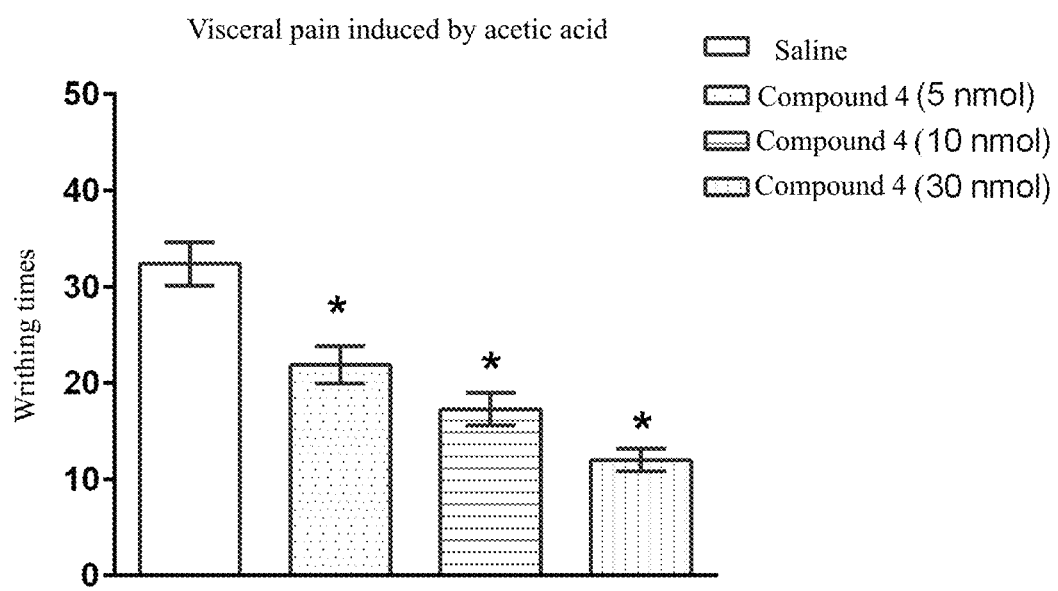
FIG. 4 illustrates analgesic effect after intrathecal injection of the compound 4 on visceral pain induced by intraperitoneal injection of acetic acid solution according to the embodiment of the present invention.

In an acetic acid-induced writhing model, mice will exhibit behaviors such as writhing, limb stretching, and abdominal pressing to the ground. The experimental results are shown in FIG. 4, the number of writhing in mice decreased with the increase of the administered dose. The compound 4 was able to significantly reduce the number of abdominal writhing in mice in a dose-dependent manner. Intrathecally injected at a dose of 30 nmol, the compound 4 inhibited the writhing behavior of mice by 63%. The ED50 of the compound 4 was 13.5 (11.88-15.34) nmol. The experimental results indicate that the compound 4 has a good inhibitory effect on acetic acid induced visceral pain.

In summary, the compounds 1-5 of the present invention can target and bind to the PD-1 receptor, which have good alleviating effect on inflammatory pain and visceral pain, and have potential application value in the preparation of analgesic drugs.

The compound 4 is selected among the embodiments of the present invention for evaluating in vitro and in vitro drug activity. The compound 4 was evaluated for drug analgesic activity by DRG neuronal calcium imaging, formalin-induced inflammatory pain modeling, and body writhing test with acetic acid. However, the application of the peptide compounds of the present invention in the preparation of analgesic drugs includes, but should not be limited to, inflammatory pain and visceral pain such as postoperative neuralgia, chemotherapy-induced pain, diabetes pain, cancer pain and other pathological pain.

Intrathecal administration of the compound 4 was preferably in the formalin test and the acetate writhing test, but it will be appreciated by those skilled in the art that the compounds described in the present patent may be suitable for a variety of administration modes, such as subcutaneous administration, caudal vein administration, lateral ventricular administration, intraperitoneal administration, and oral administration.

The foregoing are preferred embodiments of the present invention, and it should be noted that for a person of ordinary skill in the art, various improvements and modifications may be made without departing from the principles described in the present invention, and these improvements and modifications should also be covered by the protection scope of the present invention.

What is claimed is:
1. A peptide consisting of Ser Tyr Gly Gly Ala Asp Tyr Lys Arg (SEQ ID NO: 4).

* * * * *